(12) United States Patent
Srinivasan et al.

(10) Patent No.: US 9,028,413 B2
(45) Date of Patent: May 12, 2015

(54) PREDICTION-BASED FLOW ESTIMATION FOR ULTRASOUND DIAGNOSTIC IMAGING

(75) Inventors: Seshadri Srinivasan, Santa Clara, CA (US); Saurabh Datta, Cupertino, CA (US); Helene Houle, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 798 days.

(21) Appl. No.: 12/719,753

(22) Filed: Mar. 8, 2010

(65) Prior Publication Data

US 2011/0218435 A1 Sep. 8, 2011

(51) Int. Cl.
*A61B 8/06* (2006.01)
*A61B 8/08* (2006.01)
*A61B 8/00* (2006.01)

(52) U.S. Cl.
CPC . *A61B 8/06* (2013.01); *A61B 8/488* (2013.01); *A61B 8/00* (2013.01)

(58) Field of Classification Search
CPC .............. A61B 8/06; A61B 8/488; A61B 8/00
USPC .......................................... 600/407, 437–475
See application file for complete search history.

(56) References Cited

U.S. PATENT DOCUMENTS

| | | | |
|---|---|---|---|
| 4,790,321 A | 12/1988 | Miwa et al. | |
| 4,944,189 A | 7/1990 | Nakajima et al. | |
| 5,443,071 A | 8/1995 | Banjanin et al. | |
| 5,910,119 A | 6/1999 | Lin | |
| 6,277,075 B1 | 8/2001 | Torp et al. | |
| 6,350,241 B1 | 2/2002 | Lifshitz | |
| 6,859,659 B1 | 2/2005 | Jensen | |
| 7,229,412 B2 | 6/2007 | Jacob et al. | |
| 2005/0107705 A1 | 5/2005 | Pedrizzetti et al. | |
| 2005/0131300 A1* | 6/2005 | Bakircioglu et al. | 600/453 |
| 2007/0232883 A1* | 10/2007 | Ilegbusi | 600/407 |

OTHER PUBLICATIONS

Sugene, et al., *Real-time 3-Dimensional Color Doppler Flow of Mitral and Tricuspid Regurgitation: Feasibility and Initial Quantitative Comparison with 2-Dimensional Methods*, Journal of the American Society of Echocardiography, Sep. 2007, vol. 20, No. 9, pp. 1050-1057, Chicago, IL.

Matsumura, et al. *Determination of Regurgitant Orifice Area with the Use of a New Three-Dimensional Flow Convergence Geometric Assumption in Functional Mitral Regurgitation*, Journal of the American Society of Echocardiography, Nov. 2008, vol. 21, No. 11, pp. 1251-1256.

Simpson, et al., *Current Status of Flow Convergence for Clinical Applications: Is It a Leaning Tower of "PISA"?* JACC, Feb. 1996, vol. 27, No. 2, pp. 504-509.

(Continued)

*Primary Examiner* — Mark Remaly

(57) ABSTRACT

Flow estimation is provided. The flow is predicted. A mathematical, logic, machine learning or other model is used to predict flow. For example, the boundary conditions associated with a previous flow, the previous flow, and current boundary conditions are used to predict the current flow. The current flow is corrected using the predicted flow. Velocities may be unaliased based on the predicted flow. The predicted flow may replace the current flow. Prediction may additionally or alternatively be used in determination of lateral or elevational flow.

21 Claims, 6 Drawing Sheets

(56) References Cited

OTHER PUBLICATIONS

Anayiotos, et al. *Morphological Evaluation of a Reguritant Orifice by 3-D Echocardiography: Applications in the Quantification of Valvular Regurgitation*, Ultrasound in Med. & Biol., 1999, vol. 25, No. 2, pp. 209-223.

Coisne, et al. *Quantitative Assessment of Regurgitant Flow with Total Digital Three-Dimensional Reconstruction of Color Doppler Flow in the Convergent Region: in Vitro Validation*, Journal of the American Society of Echocardiography, Mar. 2002, vol. 15, No. 3, pp. 233-240.

DeGroot, et al. *Evaluation of 3-D Colour Doppler Ultrasound for the Measurement of Proximal Isovelocity Surface Area*, Ultrasound in Med & Biol., 2000, vol. 26, No. 6, pp. 989-999.

Bargiggia, et al. *A New Method for Quantitation of Mitral Regurgitation Based on Color Flow Doppler Imaging of Flow Convergence Proximal to Regurgitant Oriface*, Circulation vol. 84, No. 4, Oct. 1991, pp. 1481-1489.

Utsunomiya, et al. *Calculation of Volume Flow Rate by the Proximal Isovelocity Surface Area Method: Simplified Approach Using Color Doppler Zero Baseline Shift*, JACC vol. 22, No. 1, Jul. 1993, pp. 277-282.

Pu, et al., *Quantification of Mitral Regurgitation by the Proximal Convergence Method Using Transesophageal Echocardiography*, AHA Circulation © 1995, pp. 2169-2177.

* cited by examiner

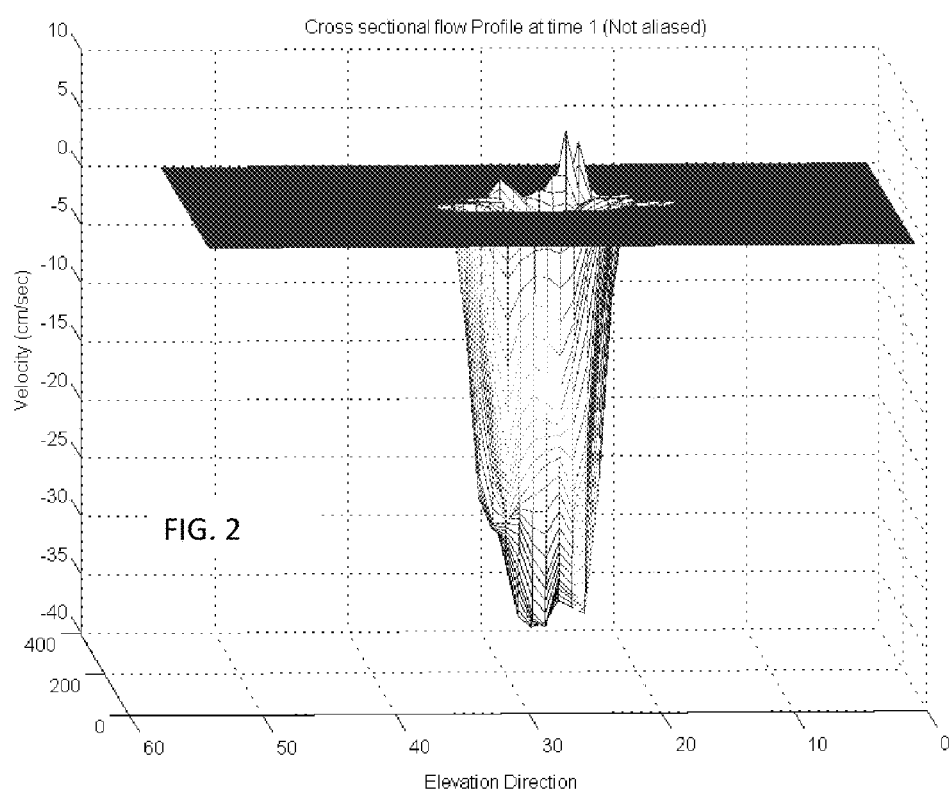

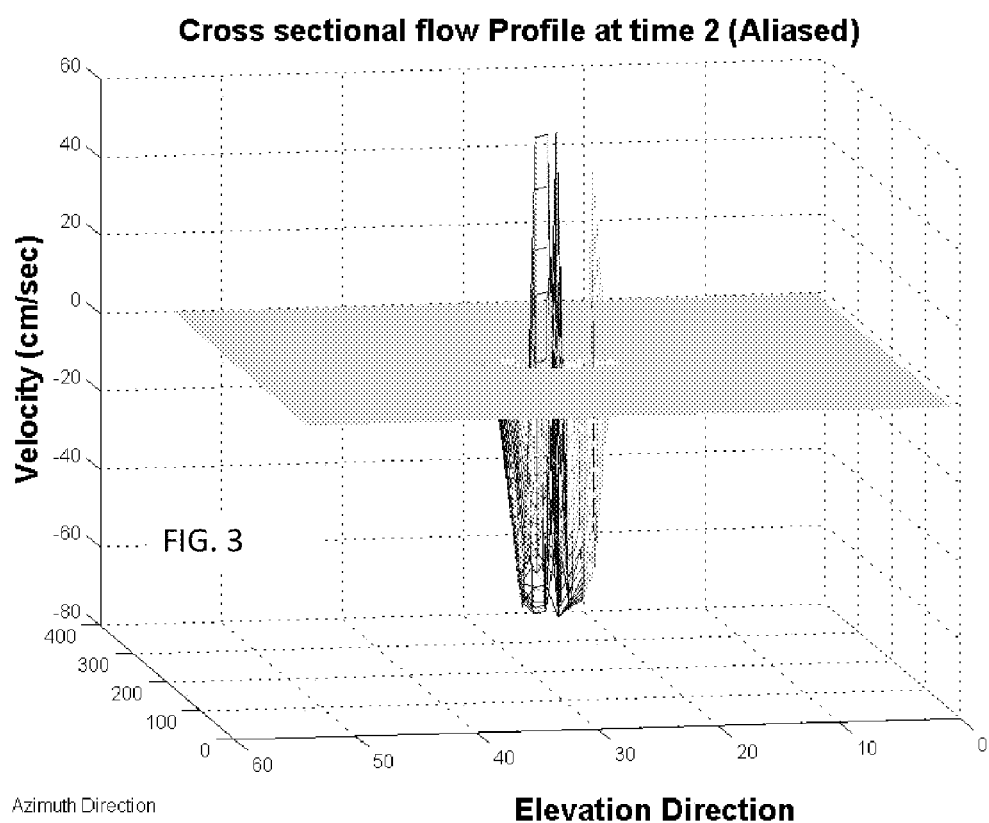

PREDICTION-BASED FLOW ESTIMATION FOR ULTRASOUND DIAGNOSTIC IMAGING

BACKGROUND

The present embodiments relate to medical diagnostic ultrasound. In particular, flow estimation is provided for medical diagnostic ultrasound.

Quantitative and qualitative images of velocity, energy, or variance depict the flow hemodynamics. Images help immediate diagnosis and also provide a trackable-methodology for short-term and long-term monitoring.

For Doppler velocity or color flow velocity imaging, a velocity scale is set. If the scale is set to be overly inclusive, then the dynamic range and sensitivity is poor. If the scale is set to narrowly, then high velocity data may be aliased (e.g., a positive velocity may appear as a negative velocity). When imaging pulsing flow, such as associated with the circulatory system, the maximum velocity varies as a function of time. Setting the velocity scale may be difficult in light of this variance.

The velocity information is an axial measurement. The velocity towards and away from the transducer along the scan line is measured. Where the flow is at an angle or not parallel with the scan line, the axial velocity may not accurately represent the speed of flow at the location.

Aliasing and/or use of axial velocity may result in inaccurate quantification. For qualitative assessment, the flow hemodynamics may be poorly or less accurately represented. The repeatability of measurements or assessment may be difficult due to different settings of the scale or scan angle.

BRIEF SUMMARY

By way of introduction, the preferred embodiments described below include a method, system, computer readable medium, and instructions for flow estimation. The flow is predicted. A mathematical, logic, machine learning, or other model is used to predict flow. For example, the previous flow, the boundary conditions associated with the previous flow, and current boundary conditions are used to predict the current flow. The estimated current flow is corrected using the predicted flow. For example, velocities may be unaliased based on the predicted flow. As another example, the predicted flow may replace the current flow. As another example, settings such as wall filter and velocity scale, are automatically adjusted for subsequent scanning. Prediction may additionally or alternatively be used in determination of lateral or elevation flow.

In a first aspect, a method is provided for flow estimation in medical diagnostic ultrasound. First velocity data representing flow in a patient is acquired at a first time. Second velocity data representing flow in the patient is acquired at a second time after the first time. A predicted flow is determined from the first velocity data. The second velocity data is corrected as a function of the predicted flow. An image of the patient is displayed as a function of the corrected second velocity data. This process may be continued for subsequent times.

In a second aspect, a computer readable storage medium has stored therein data representing instructions executable by a programmed processor for flow estimation in medical diagnostic ultrasound. The storage medium includes instructions for predicting velocity as a function of flow boundary conditions, acquiring, with ultrasound scanning of a patient, estimates of velocity representing the velocity of flow in the patient, and correcting the estimates of velocity as a function of the predicted velocity.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 2 shows an example velocity distribution with minimal or no aliasing;

FIG. 3 shows an example velocity distribution with aliasing;

DETAILED DESCRIPTION OF THE DRAWINGS AND PRESENTLY PREFERRED EMBODIMENTS

Predictive-based flow estimation may result in more accurate flow velocity information for volume quantification purposes or imaging. Predictive-based flow estimation may improve the repeatability of ultrasound color flow assessment and may reduce operator dependence of the results.

Prediction-based flow velocity estimation is provided. For predicting flow, boundary conditions, such as wall boundaries, and other criteria, such as instantaneous cavity/chamber volume, change in volume and phase of cardiac cycle are used with prior flow information to predict flow information for the current or future measured flow data. Correction, such as through comparison between the actual color data and the expected color data, may improve the low flow sensitivity (limited by the Doppler angle and wall-filter), may reduce aliasing due to the pulse repetition frequency, and may improve the reproducibility of the flow states. Lateral and elevation flow estimation is achieved using the prediction model, speckle tracking of the wall-filtered color estimates, and the actual axial velocity estimates.

In one embodiment, prediction-based flow velocity is used for aliasing correction. Current velocity estimates are unaliased based on prediction of the velocity from previous wall boundaries, current wall boundaries, chamber volume, change in volume, phase of cardiac cycle, and previous velocity estimates.

Prediction-based flow velocity angle correction may be provided. The flow data represents a two-dimensional plane or a three-dimensional volume. Quantitative assessment of flow mechanics of a three-dimensional velocity field and vorticity have the potential to expand the current understanding of cardiac flow physiology, improve quantitative accuracy and provide new short and long-term monitoring tools. An angle independent method (e.g., estimating lateral and elevation velocity as well as axial velocity) may reduce the associated velocity measurement errors.

Figure 1:
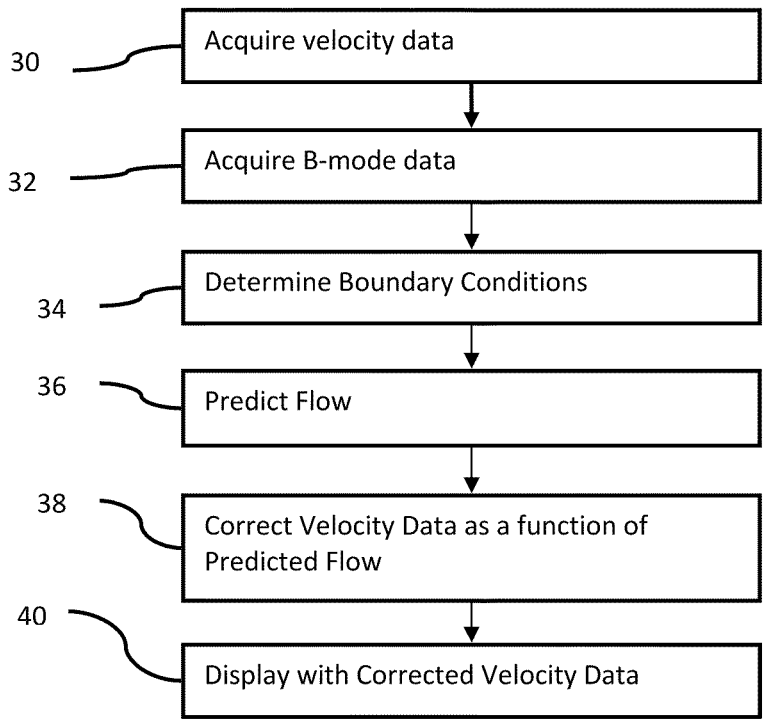
FIG. 1 is a flow chart of one embodiment of a method for flow estimation.

FIG. 1 shows a method for flow estimation in medical diagnostic ultrasound. The method is performed by the system 10 of FIG. 9 or a different system. The acts of FIG. 1 are performed in the order shown or a different order. Additional, different, or fewer acts than shown in FIG. 1 may be used. For example, acts 30, 36, and 38 are performed without any other acts. The acts of FIG. 1, described below, may be implemented in different ways. At least one example embodiment is provided below, but other embodiments are possible.

In act 30, estimates of flow are acquired with ultrasound scanning of a patient. The estimates represent flow in the scanned patient, such as flow in the heart. Estimates representing different times are acquired, such as velocity estimates representing the heart at different phases of the heart cycle or other physiologically relevant period (e.g., breathing cycle, flow-in time, or outflow time). In the sequence of estimates, some estimates are acquired prior to other estimates and other estimates are acquired after previous estimates. The previous and current estimates may be consecutive or separated by other estimates in the sequence. The current estimates may be current in the sense of just acquired or current in the sense of the estimates being examined after storage.

In optional act 32, B-mode data is acquired with ultrasound scanning of the patient. The B-mode data represents tissue associated with flow in the patient. For example, the B-mode data represents valve tissue. As another example, the B-mode data represents vessel or heart walls. The B-mode data may be acquired at the same time as the flow data or at different times. The repetition rate of acquiring B-mode may be the same or different as a repetition rate for acquiring flow data.

In acts 32 and 30, B-mode and flow ultrasound data are acquired. B-mode data represents intensities. Flow data represents estimates of velocity, energy (e.g., power), and/or variance. In one embodiment, at least velocity is estimated. The data is acquired by scanning or from memory. Data acquired from memory is previously acquired by scanning. The data is received while scanning or by transfer. In one embodiment, the data is acquired during real-time scanning (i.e., data acquired and processed in a same imaging session) or as the scanning occurs.

The ultrasound data represents a plane or volume of a patient. A volume is scanned along different planes or other distribution of scan lines within the volume. The scanned volume is an interior of an object, such as the patient. Scanning the volume provides data representing the volume, such as representing a plurality of different planes in the object (e.g., patient or heart). The data representing the volume is formed from spatial sampling of the object. The spatial samples are for locations distributed in an acoustic sampling grid in the volume. Where the acoustic sampling grid includes planar arrangements of samples, the spatial samples of the object include samples of multiple planes or slices.

Spatial samples along one or more scan lines are received. Where the transmit beam insonifies just one receive scan line, samples along that scan line are then received. Where the transmit beam insonifies multiples scan lines, then samples along the multiple scan lines are received. For example, receive beamforming is performed along at least thirty distinct receive lines in response to one broad transmit beam. To generate the samples for different receive beams, parallel receive beamformation is performed so that the different receive beams are sampled at a same time. For example, a system may be capable of forming tens or hundreds of receive beams in parallel. Alternatively, signals received from the elements are stored and sequentially processed.

Spatial samples are acquired for a plurality of receive lines in response to one and/or in response to sequential transmit beams. Using broad beam transmission, spatial samples for multiple thin slices may be simultaneously formed using dynamic receive focusing (e.g., delay and/or phase adjust and sum). Alternatively, Fourier or other processing may be used to form the spatial samples.

The scanning may be performed a plurality of times. The acts are repeated to scan sequentially different portions of the field of view. Alternatively, performing once acquires the data for the entire field of view.

The complete volume or plane is scanned at different times. Scanning at different times acquires spatial samples associated with flow. Any now known or later developed pulse sequences may be used. A sequence of at least two (flow sample count) transmissions is provided along each scan line. Any pulse repetition frequency, flow sample count, and pulse repetition interval may be used. The echo responses to the transmissions of the sequence are used to estimate velocity, energy (power), and/or variance at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

For act 30, the received spatial samples may be clutter filtered. The clutter filtering is of signals in the pulse sequence (flow sample count) for estimating motion at a given time. A given signal may be used for estimates representing different times, such as associated with a moving window for clutter filtering and estimation. Different filter outputs are used to estimate motion for a location at different times. In one embodiment, the received samples are clutter filtered to form filtered energy estimates and other energy estimates are made without clutter filtering to provide unfiltered energy estimates.

Flow data is generated from the spatial samples. Any flow data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. Color is used to distinguish from spectral Doppler imaging, where the power spectrum for a range gate is estimated. The change in frequency between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time. Multiple frames of flow data may be acquired to represent the volume or plane at different times.

The estimation is performed for spatial locations in the volume or plane. For example, velocities for the different locations are estimated from echoes responsive to the scanning.

The estimates may be thresholded. Thresholds are applied to the velocities. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

The velocity estimates acquired in act 30 may or may not be aliased. FIG. 2 shows velocities in an elevation-azimuth cross-section of a flow region. The velocities are not aliased. For example, the velocities are estimated with a scale likely to be large enough to prevent aliasing, and/or the user confirms no aliasing. In one embodiment, the velocities acquired during a lesser flow state of the heart cycle less likely associated with aliasing are assumed to not be aliased and used for initial prediction of flow.

FIG. 3 shows velocities in the elevation-azimuth cross-section of the flow region where the velocities are associated with aliasing. For example, more rapid flow occurs during a different portion of the heart cycle, resulting in aliasing where aliasing may not have occurred during other portions of the heart cycle.

The cross-sections of FIGS. 2 and 3 provide flow profiles at or adjacent to a heart valve, but may be at other locations. The flow is associated with the beginning of a jet at two different time instances. At the time instance of FIG. 2, there is no aliasing. At the later time instance of FIG. 3, aliasing occurs. The maximum velocity is limited by the velocity scale setting.

FIGS. 2 and 3 are shown for explanation purposes. Actual cross-section flow fields may not be extracted, displayed or calculated. Instead, FIG. 3 represents an undesired condition in estimates of velocity. FIG. 2 represents a desired condition. For prediction, one or more sets of velocity estimates may be assumed to be unaliased or tested and shown to be unaliased for correcting aliased flow.

B-mode data is also acquired in act 32. One of the scans used for flow data estimation or a different scan is performed. The intensity of the echoes is detected for the different spatial locations.

For the volume, some spatial locations are represented by B-mode data and other locations are represented by flow data. Thresholding or another process is performed to avoid a location being represented by both B-mode and flow data. Alternatively, one or more locations may have values for both B-mode and flow data. While both types of data together represent the volume, the different types of data may be separately stored and/or processed or may be merged into one set representing the volume.

By using broad beam transmit and receiving along a plurality of scan lines or otherwise acquiring the data for a larger sub-volume or entire volume for each transmission, more rapid scanning is provided. The more rapid scanning may allow for real-time acquisition of B-mode and color Doppler estimates. For example, the volume is scanned at least 10 times a second. In one embodiment, the volume rate is 20, 25 or other numbers of volumes per second. Each volume scan is associated with acquiring both B-mode and Doppler data. The different types of data are acquired at a substantially same time. Substantially allows for interleaving of different transmissions and/or receive processing for the different types of data. For example, ten or more volumes of data are acquired each heart cycle where each volume includes B-mode and velocity data representing a generally same portion (e.g., within $1/10^{th}$ of the heart cycle of each other) of the heart cycle. In alternative embodiments, the rate of acquisition for B-mode data is greater than or less than for color flow data.

In act 34, boundary conditions are determined. The boundary conditions are boundaries for flow or flow boundary conditions. The boundary conditions are used to predict flow. In other embodiments, boundary conditions are not determined, such as where flow is predicted based on other factors.

The flow boundaries are of a flow structure and/or tissue structure. For flow structure, velocity, energy, variance, vorticity, or other estimation may be used to determine the flow structure. A threshold, edge detection, modeling, template matching, or other process may indicate the area or volume of the flow structure. For tissue structure, threshold, edge detection, modeling, template matching, or other process may be used to detect the tissue boundaries (e.g., borders or edges) from B-mode data. With B-mode data, borders or edges may be detected with a gradient process.

A combination of flow and tissue structure or of multiple tissue or multiple flow structures may be formed. For example, the flow structure and tissue structure may have similar borders. The borders are averaged, interpolated or otherwise combined to create the boundary conditions. Alternatively, quantities determined from the different borders are combined (e.g., averaged).

In one embodiment, boundary conditions are extracted using unfiltered energy estimates. A sequence of unfiltered energy estimates representing a volume at different times is used for wall motion tracking. Using the unfiltered energy may be a faster way of obtaining the boundary conditions than using B-mode data. In alternative embodiments, B-mode data is used.

For each volume of unfiltered energy, edge identification is performed on binarized color velocity data. A threshold is applied to the velocity data to form binary data (i.e., above or below the threshold). A gradient or other process may be used to find the border of the velocity structure defined by the binary data.

The unfiltered energy data is thresholded. Borders are determined as locations with higher unfiltered energy and lower velocity or higher unfiltered energy and higher velocity gradient. Such identified borders are used to refine the borders of the binary velocity data.

In an optional embodiment, B-mode or other tissue structure is used to refine the border detected from the unfiltered energy estimates. B-mode data may have a higher resolution, allowing a more precisely determined boundary. Borders may be detected from B-mode data using any edge detection, such as thresholding or gradient detection. Where the B-mode and energy borders are sufficiently different, the B-mode border is used. For similar border locations, the energy border is used. The B-mode and flow borders may be combined, such as by interpolation or averaging.

In another optional embodiment, contrast agent imaging is used to refine the unfiltered energy borders. Borders identified using contrast agent imaging can be combined with flow borders. Tissue specific harmonic imaging or cubic fundamental-based imaging may be used for border detection. Cubic fundamental-based imaging may derive tissue response with the presence of contrast agents.

In another embodiment, surface-enhanced B-mode boundaries are obtained using color edges and B-mode edges. A threshold is applied to unfiltered energy. Values above the threshold are set to 1 and values below are set to 0, providing a binary image. Edges of contiguous regions in the binary information are identified. Any edge detection may be used, such as skeletonization or other morphological method. The orientation of the edges or region is determined, such as identifying a major axis of the largest contiguous region.

Skeletonization, other morphological methods, gradient based, or other edge detection is applied to the B-mode data.

The B-mode edges and color edges are compared. Any differences may be interpolated, morphed, or otherwise combined to find an overall border or edge. B-mode surfaces based on the B-mode data at the border or edge pixels are identified.

The B-mode, flow or other border may be combined or used with other references. For example, a model of the heart at different phases is fit to the detected edges. The edges are morphed to more closely match the model, such as using a spring or other cost function.

The determined surfaces are used as the boundary conditions. Alternatively, the surfaces are used to calculate a boundary condition. In one embodiment, the boundary condition is a volume in the patient, such as the volume of a heart chamber. The volume of the heart chamber, flow region, or other flow or tissue structure in the patient is calculated from the borders as the boundary condition.

The boundary condition may be determined for different times. For example, the heart changes shape throughout a cycle. The volume of a heart chamber at different times is calculated. In the example represented by FIGS. 2 and 3, a volume is determined for a heart chamber at the time instance represented by FIG. 2 and another volume is determined for the heart chamber at the time instance represented by FIG. 3.

In act 36, the flow is predicted. For example, velocity is predicted. Other flow information may be predicted, such as the energy, variance, vorticity, flow reversal, rate, volume, change in value, average, maximum, minimum, or integral of flow. The predicted flow is an instantaneous value, such as predicting flow at a given time. In other embodiment, flow value over time or flow value per heart cycle is predicted. One or more characteristics of flow hemodynamics are predicted.

The flow is predicted for each spatial location in a region of interest (e.g., each spatial location within the flow boundaries). In alternative embodiments, the flow is predicted for multiple locations, such as predicting a maximum or an average velocity for the entire region of interest or for each of the plurality of sub-regions.

The flow is predicted using any information. Any model of flow may be used for the prediction. The model may be a machine learned model, a morphological model, a model of operation of an organ, or a mathematical model.

In one embodiment, the flow is predicted as a function of the flow boundary conditions. The boundary conditions limit the flow. For example, the shape, location, size, or other boundary information may dictate or influence the velocity. The velocity is predicted based on the boundary condition as an input feature.

The flow may be predicted based on information for a current time, previous information, or combinations of both. For example, the current conditions are used to predict the current flow. As another example, previous flow and current conditions, such as boundary conditions, are used to predict the current flow. In yet another example, flow and boundary conditions from a plurality of previous times are used to predict future flow. A trend of previous flow may be used to predict future or current flow. The flow throughout a previous heart cycle may be used.

Figure 7:
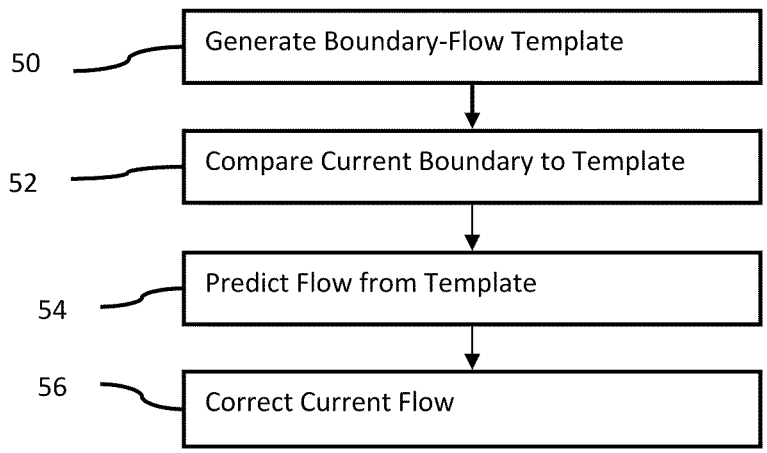
FIG. 7 is a flow chart of another embodiment of a method for flow estimation.

In one embodiment, the flow is predicted as a function of previous flow, boundary conditions associated with the previous flow, and current boundary conditions. FIG. 7 shows one embodiment of prediction to correct flow based on comparison. A boundary condition template is formed in act 50. The template is formed from a model of organ performance for from previous data. Act 30-38 of FIG. 1 are performed for one or more heart cycles to form a template in another embodiment. Different boundary conditions are provided in the template for different phases of the heart cycle. In act 52 of FIG. 7, the flow states and/or boundary conditions of prior times are used by comparing with a database of possible flow states and boundary conditions to compute the predicted flow state in act 54. The current boundary conditions are in a different heart cycle, such as a subsequent heart cycle. The current boundary conditions are compared with the template of the boundary conditions obtained during the current and previous cardiac cycles or modeled from different patients. The closest match between boundary conditions and/or previous flow is identified. The flow state is predicted from the closest match, from interpolation of multiple closely matching boundary conditions, or from extrapolation from one or more close matches.

Returning to act 36 of FIG. 1, a numerical or mathematical flow simulation model may be used. For example, a velocity at one time is predicted as a function of the volume of a chamber at that one time, the volume of the chamber at a previous time, and the velocity at the previous time. The difference in the two volumes equals the additional inflow through the valve. Therefore, $Vol(t2)-Vol(t0)=[Vel(t1)-Vel(t2)]*Area(t1)*(t2-t1)$. The velocity is an average or maximum in a cross-section through a flow structure. The area is of the cross-section. The volume is of the flow structure, such as a jet volume or chamber volume. From this equation, the velocity at t2 is predicted from velocity at t1. Other mathematical models may be used.

Figure 4:
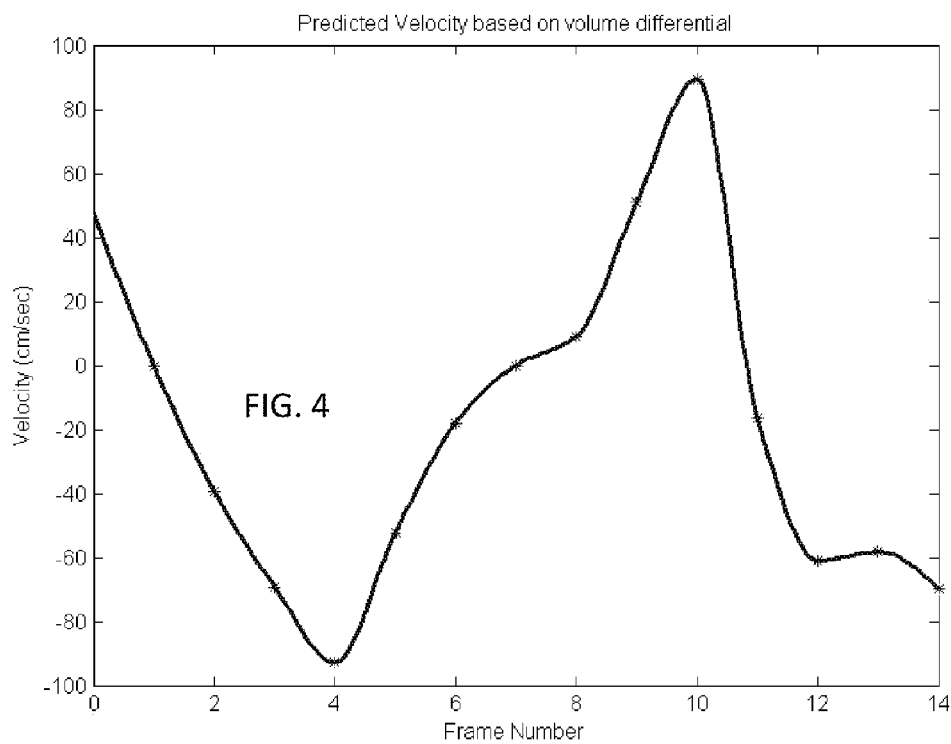
FIG. 4 is a graph of predicted velocity as a function of time or frame, according to one embodiment.

The original prediction is based on unaliased velocities or velocities assumed to be unaliased. As the process continues, the later acquired velocities are unaliased, and the unaliased velocities are used for further predictions. FIG. 4 shows the predicted flow velocity as a function of time or frame number. The predicted velocity is the maximum or average velocity for a flow structure. The velocity for any given frame is predicted from the corrected velocity of the frame before and the boundary conditions (e.g., volume) of the current and previous frames.

The prediction technique or model may change over time, such as using the mathematical model for one or more heart cycles. The actual velocity after correction and/or boundary conditions are stored as a template. For later heart cycles, the comparison model is used. The current boundary condition and/or flow are compared to the template. A closest match is used to predict the velocity. For example, the current boundary condition and heart cycle phase are used to identify a similar boundary condition at a similar phase. The velocity associated with the similar situation is used as the predicted velocity and/or used to derive the predicted velocity. Interpolation of the boundary conditions may provide a faster way of predicting the flow state.

In act 38 of FIG. 1 and act 56 of FIG. 7, the flow is corrected as a function of the predicted flow. For example, estimates of velocity are corrected based on predicted velocity. The predicted velocity may be for a region, and the velocity estimates for different locations are corrected, if appropriate, based on the same predicted velocity.

Any correction may be used. For example, the predicted velocity is compared to a velocity scale. If the predicted velocity is greater than or close to the maximum velocity of the velocity scale, at least some of the current velocity estimates are assumed to be aliased. The data may be unaliased using any process, such as identifying estimates associated with large gradient and extrapolating the value beyond the velocity scale.

In one embodiment, the flow is corrected based on a comparison. For example, the current velocity data is processed to remove aliasing. If the current axial velocity is of the opposite sign as the predicted velocity, aliasing is assumed to have occurred. The pulse repetition frequency or velocity scale is low, causing aliasing. The scale may be increased for future estimates. For the current estimate, velocity anti-aliasing is performed for the current axial velocity.

Figure 5:
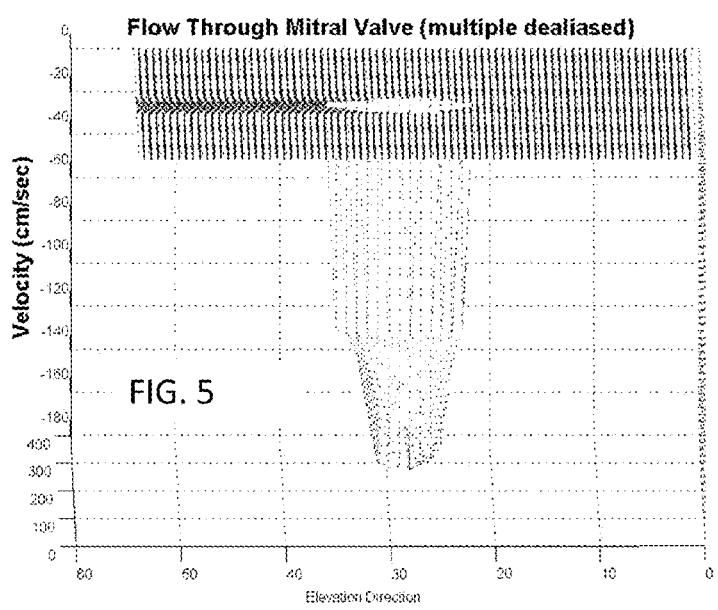
FIG. 5 shows an example velocity distribution of FIG. 3 after unaliasing as a function of the predicted flow.

In one embodiment, the anti-aliasing at time instance t2 is done using the predicted velocity at t2, the velocity profile at t1 (see FIG. 2), and the actual aliased velocity at t2 (see FIG. 3). By changing the sign of the velocity and adding the estimate to the maximum velocity, an aliased velocity is unaliased. FIG. 5 shows the de-aliased flow profile at time instance t2 after correcting the aliased flow profile shown at FIG. 3.

Figure 6:
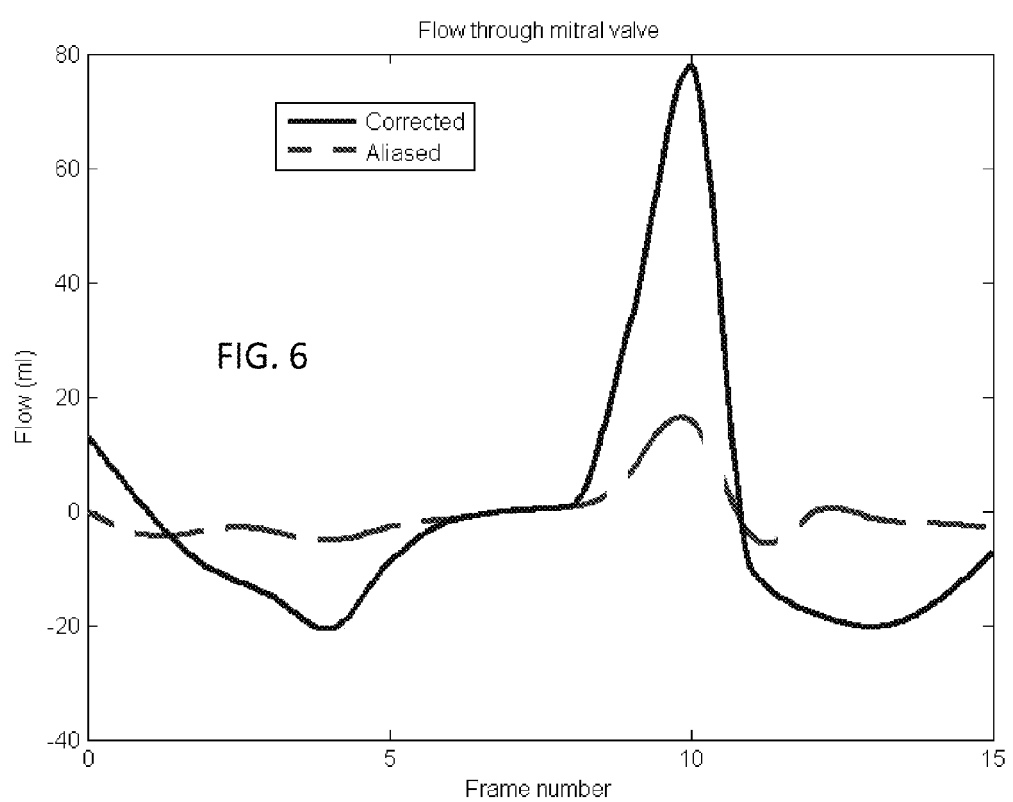
FIG. 6 shows example volume rate through a valve calculated with and without the prediction-based correction.

FIG. 6 shows the volume rate calculated across (e.g., cross-section) a valve. The volume rate is computed as the integral of velocity for a cross-section or area. The flow may be calculated as the integral of volume rate over time. For the aliased data, the correction based on prediction is not used. For the corrected data, the correction based on the prediction is used. The correction results in a more accurate volume rate. The corrected volume rate corresponds well with the pathological condition.

Other corrections may be used instead of or in addition to anti-aliasing. For example, the current velocity estimate may be replaced with a predicted velocity. An estimated cross-sectional flow profile may be used to correct velocities at a particular location as a weighting function. If the axial velocity is zero and the predicted flow is non-zero, the axial velocity is replaced with the predicted axial velocity. This situation may occur due to either the Doppler angle being generally orthogonal to the flow or the wall filter cut-off being overly aggressive. If the lateral and elevation velocities are zero, the velocities are replaced with the predicted lateral and elevation velocities. The lateral and elevation velocities may be inaccurate due to lack of adequate scatterer strength or small motion caused by a high pulse repetition frequency.

In other embodiments, the estimation and/or scanning are altered. The alteration is for reprocessing received signals or for processing signals received in the future. For example, a setting of a wall filter for estimating velocity data adapts to be more or less sensitive based on the predicted flow. The velocity scale may adapt based on the predicted or corrected velocities.

In act 40, an image is displayed. The image represents the flow, such as being a color velocity or energy image. The flow data may be overlaid or displayed with B-mode or tissue data. The image is a function of the corrected flow data. In one embodiment, the image is a rendering from corrected velocity data representing a volume. Two-dimensional images may be provided. A sequence of images may be provided.

In one embodiment, a quantity is calculated from the corrected flow data and displayed with or without images. The quantity is displayed as a value, number, graph, color modulation, or text. As a sequence of images is viewed, the quantities associated with the given volume or data is displayed. For example, the corrected volume flow of FIG. 6 is displayed as a graph. The graph is of the quantity as a function of time, such as throughout one or more cardiac cycles.

Figure 8:
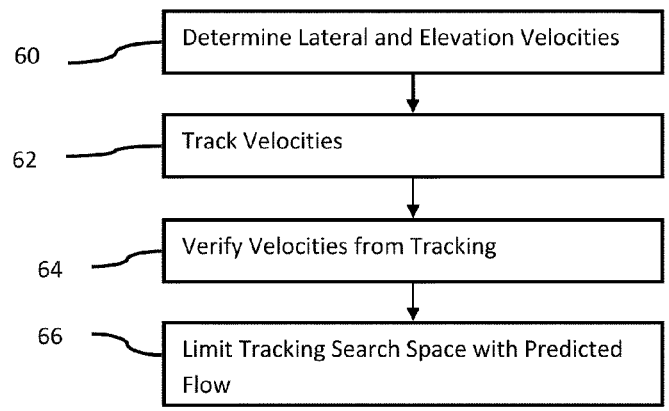
FIG. 8 is a flow chart of yet another embodiment of a method for flow estimation.

The prediction and correction may be performed for axial, lateral, and/or elevation flow. In one embodiment, only axial flow estimation is performed as described above for FIG. 1. FIG. 8 shows one embodiment of a method for flow estimation for lateral (i.e., azimuth) and elevation flow. Additional, different, or fewer acts may be provided.

In act 60, the lateral and/or elevation velocities are determined. The determination is made, in part, by performing the tracking of act 62. In act 60, the signals from each transmission in the flow sample count are phase rotated. The phase rotation occurs after wall filtering. Along the axis of reception, the samples are phase rotated based on the corrected axial velocity to have a common phase. Energy signals are estimated using the phase-rotated signals. The original signals or signals without phase rotation are also used without wall filtering to estimate energy signals. This provides two versions of axial energy estimates.

In act 62, the lateral and elevation velocities are determined by tracking. For a volume set of data, a 3D-kernel (window) is used to track the filtered and unfiltered energy signals over the flow sample count. The energy estimates from one time are tracked relative to energy estimates at another time Such a tracking using the 3D kernel can be within the flow sample count or between frames. Tracking is performed using cross-correlation, sum of absolute differences, or other measure of similarity. Any search space may be used. By translating and/or rotating the data of the window in one set to different positions in another set, the offset in three dimensions is provided. The offset and time difference indicate the velocity. The velocity is a three-dimensional vector, including lateral and elevation components.

In act 64, the lateral and elevation velocities are verified. The axial, lateral and elevation velocity estimates of the unfiltered energy are compared with that of the filtered energy. If the velocities are within a threshold amount of each other in the lateral and elevation directions or in three directions, then the lateral and elevation velocities are set as the estimated lateral and elevation velocities from either the filtered or unfiltered energy tracking. If the relationship is not comparable (the velocity difference between the filtered and unfiltered energies exceed the threshold), then alternate firings in the flow sample count are used and acts 60 and 62 are repeated. Alternate firings include selecting a different group of samples to be used for estimating the energy. For example, the original samples used to estimate a given energy value are a1, a2, a3, a4, a5, a6 . . . . Alternate firings may include regular alternates, such as every other (e.g., a1, a3, a5 . . . ), every third (e.g., a2, a5, . . . or a1, a4, . . . ) or other different groupings from the original. Using the alternate flow sample count may improve the robustness of the lateral and elevation velocity estimation.

In act 66, the predicted velocity is used in the estimation of lateral and elevation velocity. The estimates are corrected by limiting the estimation process. For example, the predicted axial velocity determined in act 36 of FIG. 1 is used to limit the search space for tracking in act 62 of FIG. 8. As another example, the lateral and elevation velocities are predicted, such as using the boundary conditions and previous lateral and elevation velocities to predict the current or future lateral and elevation velocity. The search space for tracking is then set to be less than all of the volume or plane, such as set to be twice a distance determined from the predicted velocities. The direction of displacement of the search space, the pattern of the search (e.g., coarse and fine searching), or other search characteristic may be limited by the predicted flow. Limiting the search space may reduce the amount of processing needed and avoid errors from local maxima or minima in the similarity measure.

Figure 9:
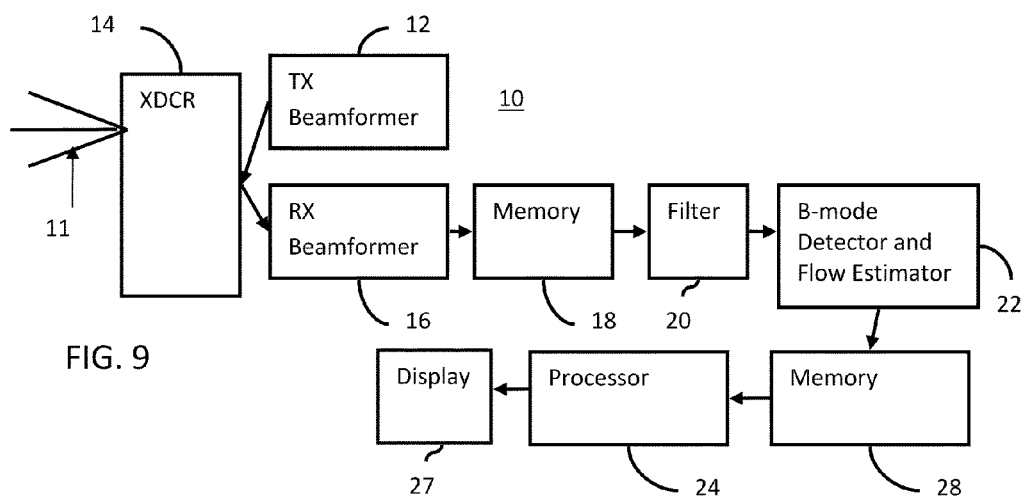
FIG. 9 is a block diagram of one embodiment of a system for flow estimation.

FIG. 9 shows one embodiment of a system 10 for flow estimation in medical diagnostic ultrasound. The system 10 includes a transmit beamformer 12, a transducer 14, a receive beamformer 16, a memory 18, a filter 20, a B-mode detector and flow estimator 22, a memory 28, a processor 24, and a display 27. Additional, different or fewer components may be provided. For example, the system includes the B-mode detector and flow estimator 22 and processor 24 without the front-end components, such as the transmit and receive beamformers 12, 16. In one embodiment, the system 10 is a medical diagnostic ultrasound system. In an alternative embodiment, the system 10 is a computer or workstation. In yet another embodiment, the B-mode detector and flow estimator 22 are part of a medical diagnostic ultrasound system or other medical imaging system, and the processor 24 is part of a separate workstation or remote system.

The transducer 14 is an array of a plurality of elements. The elements are piezoelectric or capacitive membrane elements. The array is configured as a one-dimensional array, a two-dimensional array, a 1.5 D array, a 1.25 D array, a 1.75 D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. In one embodiment, the transmit beamformer 12 transmits beams sufficiently large to cover at least thirty distinct receive lines, and the receive beamformer 16 receives along these distinct receive lines in response to the transmit beam. Use of the broad beam transmit and parallel receive beamforming along tens or hundreds of receive lines allows for real-time scanning of multiple slices or a volume. The receive lines and/or transmit beams are distributed in the volume, such as the receive lines for one transmit being in at least two different planes. The receive beamformer 16 samples the receive beams at different depths. Sampling the same location at different times obtains a sequence for flow estimation. Two-dimensional scanning may be provided.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more (e.g., 30, 40, or 50) receive beams in response to each transmit beam. The receive beams are collinear, parallel and offset or non-parallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for a substantially same spatial location. Phase changes between the different receive events indicate the velocity of the tissue or fluid. A velocity sample group corresponds to multiple transmissions for each of a plurality of scan lines 11. The number of times a substantially same spatial location, such as a scan line 11, is scanned within a velocity or flow sample group is the velocity or flow sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a three-dimensional grid.

The filter 20 is a clutter (e.g., wall) filter, finite impulse response filter, infinite impulse response filter, analog filter, digital filter, combinations thereof, or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 identifies velocity information from slower moving tissue as opposed to fluids or alternatively reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The B-mode detector and flow estimator 22 is a Doppler processor or cross-correlation processor for estimating the flow data and a B-mode detector for determining the intensity. In alternative embodiments, another device now known or later developed for estimating velocity, energy, and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The energy and variance may also be calculated.

Flow data (e.g., velocity, energy, or variance) is estimated for spatial locations in the scan volume or plane from the beamformed scan samples. For example, the flow data represents a plurality of different planes in the volume.

The flow estimator 22 may apply one or more thresholds to identify sufficient motion information. For example, velocity and/or energy thresholding for identifying velocities is used. In alternative embodiments, a separate processor or filter applies thresholds. The B-mode detector and flow estimator 22 outputs B-mode and flow data for the volume.

The memory 28 is video random access memory, random access memory, removable media (e.g. diskette or compact disc), hard drive, database, or other memory device for storing B-mode and flow data. The stored data is in a polar or Cartesian coordinate format. The memory 28 is used by the processor 24 for the various filtering, predictions, corrections, calculations or other acts described for FIGS. 1, 7, and 8. The processor 24 may additionally reformat the data, such as interpolating the data representing the volume to a regularly spaced Cartesian coordinate three-dimensional grid.

The display 27 is a CRT, LCD, plasma, projector, monitor, printer, touch screen, or other now known or later developed display device. The display 27 receives RGB or other color values and outputs an image. The image may be gray scale or color image. The image represents the region of the patient scanned by the beamformer and transducer 14.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 and/or other components of the system 10 operate pursuant to instruction provided in the memory 18, 28, or a different memory for flow estimation in medical diagnostic ultrasound.

The processor 24 receives B-mode and flow data from the B-mode detector and flow estimator 22, the memory 28, and/or another source. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 calculates one or more quantities and/or causes generation of an image, such as a two-dimensional image representing a volume from a viewing direction. The image is rendered from B-mode and flow data. The rendering is performed using rendering parameters. One or more of the rendering parameters may have adaptive values. For example, the values are different for different locations. Along a ray line for rendering, the opacity and/or fade may have different values depending on the B-mode and flow data along the ray line.

The instructions for implementing the processes, methods and/or techniques discussed above are provided on computer-readable storage media or memories, such as a cache, buffer, RAM, removable media, hard drive or other computer readable storage media. In one embodiment, the instructions are for flow estimation. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for flow estimation in medical diagnostic ultrasound, the method comprising:

acquiring, by scanning a patient with ultrasound, an estimated first velocity representing flow at a first location in the patient at a first time;

acquiring, by scanning a patient with ultrasound, an estimated second velocity representing flow at the first location in the patient at a second time after the first time;

determining a predicted estimate of a third velocity from the first velocity, the predicted estimate being a specific value other than a maximum or minimum velocity and being for the first location at the second time;

correcting the second velocity as a function of the predicted third velocity, the correcting changing an existing velocity value of the second velocity to another velocity value; and displaying an image of the patient as a function of the corrected second velocity.

2. The method of claim 1 wherein correcting comprises unaliasing the second velocity.

3. The method of claim 1 wherein correcting comprises replacing the second velocity with a predicted velocity.

4. The method of claim 1 further comprising an additional act of adapting a setting of a wall filter, the wall filter for filtering receive data used for estimating fourth velocity.

5. The method of claim 1 wherein determining comprises determining the predicted flow as a function of predicted velocity.

6. The method of claim 1 wherein determining comprises determining the predicted flow as a function of the first velocity and boundary conditions associated with the flow in the patient.

7. The method of claim 6 further comprising:
acquiring tissue data representing tissue associated with the flow in the patient; and
determining the boundary conditions from the tissue data.

8. The method of claim 6 further comprising determining the boundary conditions from energy data representing energy of the flow.

9. The method of claim 6 further comprising determining the boundary conditions as a first volume defined by a surface at the first time and a second volume defined by the surface at the second time, and wherein determining the predicted flow comprises predicting a third velocity at the second time as a function of the first and second volumes and the first velocity.

10. The method of claim 6 further comprising:
acquiring contrast data representing tissue associated with the flow in the patient; and
determining the boundary conditions from the contrast data.

11. The method of claim 1 wherein determining and correcting occur during an anatomically relevant period of interest;
further comprising:
generating a template of boundary conditions of the heart, the boundary conditions generated for different phases of the first period of interest;
comparing a current boundary condition with the template;
predicting a flow state based on the comparing; and
performing correction as a function of the predicted flow state.

12. The method of claim 1 wherein determining the predicted flow comprises determining first lateral and elevation velocities with tracking, the tracking indicating a spatial offset over a period, the first lateral and elevation velocities being a function of the spatial offset and the period; and
wherein correcting comprises limiting a search space for the tracking based on the first lateral and elevation velocities.

13. In a non-transitory computer readable storage medium having stored therein data representing instructions executable by a programmed processor for flow estimation in medical diagnostic ultrasound, the storage medium comprising instructions for:
predicting velocity of flow of fluid for locations in a fluid region, the velocity predicted from flow boundary conditions, the flow boundary conditions including a boundary of the fluid region;
acquiring, with ultrasound scanning of a patient, estimates of velocity representing the velocity of flow at the locations in the patient; and
correcting the estimates of velocity as a function of the predicted velocity, the correcting changing an existing velocity value of the estimates of velocity to another velocity value.

14. The non-transitory computer readable storage medium of claim 13 wherein correcting comprises unaliasing the estimates of velocity.

15. The non-transitory computer readable storage medium of claim 13 wherein correcting comprises replacing the estimate of velocity with the predicted velocity.

16. The non-transitory computer readable storage medium of claim 13 wherein predicting comprises determining the predicted velocity as a function of previous velocity data acquired with ultrasound scanning of the patient and the flow boundary conditions, the flow boundary conditions being in the patient.

17. The non-transitory computer readable storage medium of claim 16 further comprising:
acquiring B-mode data representing tissue in the patient; and
determining the flow boundary conditions with the tissue data.

18. The non-transitory computer readable storage medium of claim 16 further comprising: determining the flow boundary conditions from energy data.

19. The non-transitory computer readable storage medium of claim 16 further comprising:
determining the flow boundary conditions as a first volume at a first time and a second volume at a second time, wherein the estimates of velocity are acquired at the second time, and wherein predicting comprises predicting the predicted velocity at the second time as a function of the first and second volumes and previous estimates of velocity acquired, with ultrasound scanning of the patient, at the first time.

20. The non-transitory computer readable storage medium of claim 13 wherein predicting, acquiring, and correcting occur during a first heart cycle;
further comprising:
generating a template of boundary conditions of the heart, the boundary conditions generated for different phases of the first heart cycle;
comparing a current boundary condition with the template, the current boundary condition being in a second heart cycle after the first heart cycle;
predicting a flow state based on the comparison; and
performing correction as a function of the predicted flow state.

21. The non-transitory computer readable storage medium of claim 13 wherein determining the predicted flow comprises determining first lateral and elevation velocities with tracking, the tracking indicating a spatial offset over a period, the first lateral and elevation velocities being a function of the spatial offset and the period; and
wherein correcting comprises limiting a search space for the tracking based on the first lateral and elevation velocities.

* * * * *